United States Patent [19]

Coy et al.

[11] Patent Number: 5,888,963
[45] Date of Patent: Mar. 30, 1999

[54] TREATMENT OF BONE DISORDERS WITH ADRENOMEDULLIN

[75] Inventors: David H. Coy, New Orleans, La.; Jillian Cornish, Mission Bay, New Zealand; Ian Reginald Reid, Mt. Albert, New Zealand; Garth James Smith Cooper, Herne Bay, New Zealand

[73] Assignees: Auckland UniServices Limited, Auckland, New Zealand; The Administrators of The Tulane Educational Fund, New Orleans, La.

[21] Appl. No.: 634,562

[22] Filed: Apr. 18, 1996

[51] Int. Cl.$^6$ ............................ A01N 37/18; C07K 14/00; C07K 14/51

[52] U.S. Cl. ............................ 514/2; 514/12; 424/198.1; 424/422; 424/434; 530/300; 530/324; 530/325; 530/336; 530/326; 930/10

[58] Field of Search ............................ 424/434, 422, 424/198.1; 514/2, 12; 530/300, 324, 325, 333, 326; 930/10

[56] References Cited

U.S. PATENT DOCUMENTS 5,478,847  12/1995  Draper .

FOREIGN PATENT DOCUMENTS 0 622 458 A2  11/1994  European Pat. Off. .

OTHER PUBLICATIONS

DeWitt et al. (1994) Eurp. J. Pharmacol. 257, 303–306.
Cornish et al (1995) BBRC 207(1), 133–139.
Cheng et al., "Synthetic Human Adrenomedullin and ADM15–52 Have Potent Short–Lasting Vasodilator Activity In the Pulmonary Vascular Bed of the Cat", Life Sciences 55:PL251–PL256, 1994.
Eguchi et al., "Structure–Activity Relationship of Adrenomedullin, a Novel Vasodilatory Peptide, in Cultured Rat Vascular Smooth Muscle Cells", Endocrinology 135:2454–2458, 1994.
Hao et al., "An Adrenomedullin (ADM) Fragment Retains the Systemic Vasodilator Activity of Human ADM", Life Sciences 54:PL265–PL270, 1994.
Ichiki et al., "Distribution and Characterization of Immunoreactive Adrenomedullin in Human Tissue and Plasma", FEBS Letters 338:6–10, 1994.
Ishiyama et al., "Hemodynamic Effects of a Novel Hypotensive Peptide, Human Adrenomedullin, In Rats", European Journal of Pharmacology 241:271–273, 1993.
Kanazawa et al., "Adrenomedullin, A Newly Discovered Hypotensive Peptide, Is a Potent Bronchodilator", 205:251–254, 1994.
Kitamura et al., "Adrenomedullin: A Novel Hypotensive Peptide Isolated From Human Pheochromocytoma", Biochemical & Biophysical Research Comm. 192:553–560, 1993.
Kitamura et al., "Cloning and Characterization of cDNA Encoding a Precursor for Human Adrenomedullin", Biochemical and Biophysical Research Comm. 194:720–725, 1993.
Kitamura et al., "Complete Amino Acid Sequence of Porcine Adrenomedullin and Cloning of cDNA Encoding its Precursor", FEBS Letters 338:306–310, 1994.
Lin et al., "An Adrenomedullin Fragment Retains the Systemic Vasodepressor Activity of Rat Adrenomedullin", European Journal of Pharmacology 260:1–4, 1994.
Lippton et al., "Adrenomedullin Dilates the Pulmonary Vascular Bed In Vivo", J. Appl. Physiol. 76:2154–2156, 1994.
Muff et al., "Calcitonin, Calcitonin Gene–related Peptide, Adrenomedullin and Amylin: Homologous Peptides, Separate Receptors and Overlapping Biological Actions", European Journal of Endocrinology 133:17–20, 1995.
Nuki et al., "Vasodilator Effect of Adrenomedullin and Calcitonin Gene–Related Peptide Receptors In Rat Mesenteric Vascular Beds", Biochemical and Biophysical Research Comm 196:245–251, 1993.
Owji et al., "An Abundant and Specific Binding Site for the Novel Vasodilator Adrenomedullin in the Rat", Endocrinology 136:2127–2134, 1995.
Perret et al., "The Effect of Adrenomedullin on the Isolated Heart", Life Sciences 53:PL377–379, 1993.
Sakata et al., "Molecular Cloning and Biological Activities of Rat Adrenomedullin, A Hypotensive Peptide", Biochemical and Biophysical Research Comm. 195:921–927, 1993.
Santiago et al., "Comparison of Responses to Adrenomedullin and Adrenomedullin Analogs in the Mesenteric Vascular Bed of the Cat", European Journal of Pharmacology 272:115–118, 1995.
Santiago et al., "Synthetic Human Adrenomedullin and Adrenomedullin 15–52 Have Potent Short Lived Vasodilator Activity in the Hindlimb Vascular Bed of the Cat", Life Sciences 55:PL85–PL90, 1994.
Zimmermann et al., "Adrenomedullin and Calcitonin Gene–Related Peptide Interact With the Same Receptor in Cultured Human Neuroblastoma SK–N–MC Cells", Peptides 16:421–424, 1995.

*Primary Examiner*—Paula K. Hutzell
*Assistant Examiner*—Khalid Masood
*Attorney, Agent, or Firm*—Fish & Richardson P.C.

[57] ABSTRACT

A method for promoting bone growth in a patient (e.g., a mammal such as a human) said method including the step of administering a therapeutically effective amount of adrenomedullin or an adrenomedullin agonist to said patient.

20 Claims, No Drawings

TREATMENT OF BONE DISORDERS WITH ADRENOMEDULLIN

BACKGROUND OF THE INVENTION

Adrenomedullin is a 52-amino acid peptide first described in 1993 (Kitamura, et al., Biochem. Biophys. Res. Commun. 192:553–560 (1993)). It was originally identified in a human pheochromocytoma and has since been found to be in normal adrenal medulla and in many other tissues including the atria, ventricles, endothelial cells, lungs, brain and kidneys (Kitamura, K., et al., Biochem. Biophys. Res. Commun. 192:553–560 (1993); Kitamura, K., et al., Biochem. Biophys. Res. Commun. 192:720–725 (1993); Ichiki, Y., et al., FEBS Lett. 338:6–10 (1994); Katoh, F., et al., FEBS Lett. 348:61–64 (1994); Sakata, J., et al., Biochem. Biophys. Res. Commun. 195:921–927 (1993); Sugo, S., et al., Biochem. Biophys. Res. Commun. 201:1160–1166 (1994); Sugo, S., et al., Biochem. Biophys. Res. Commun. 203:719–726 (1994); Jougasaki, M., et al., Am. J. Physiol. 268:F657–F663 (1995); Satoh, F., et al., J. Clin. Endocrinol. Metab. 80:1750–1752 (1995); and Jougasaki, M., et al., Circulation 92:286–289 (1995)). It circulates in picomolar concentrations in both rats and man (Kitamura, K., et al., FEBS Lett. 341:288–290 (1994); Sakata, J., et al., FEBS Lett. 352:105–108 (1994); Sato, K., et al., Life Sci. 57:189–194 (1995)). It is a potent vasodilator, acting directly on the renal, cerebral, mesenteric, pulmonary, and systemic circulations, and its administration results in hypotension (Seguchi, H., et al., Biochem. Biophys. Res. Commun. 215:619–625 (1995); Nuki, C., et al., Biochem. Biophys. Res. Commun. 196:245–251 (1993); Berthiaume, N., et al., Can. J. Physiol. Pharmacol. 73:1080–1083 (1995); Nakamura, K., et al., Jpn. J. Pharmacol. 67:259–262 (1995); Feng, C. J., et al., Life Sci. 55:PL433–PL438 (1994); and DeWitt, B. J., et al., Eur. J. Pharmacol. 257:303–306 (1994). Its hemodynamic effects are probably mediated via receptors on vascular smooth muscle cells and possibly endothelial cells (Ishizaka, Y., et al., Biochem. Biophys. Res. Commun. 200:642–646 (1994); Eguchi, S., et al., FEBS Lett. 340:226–230 (1994); and Shimekake, Y., et al., J. Biol. Chem. 270:4412–4417 (1995)). Binding to renal tubular membranes has been observed, and sodium, potassium, and water excretion are increased by adrenomedullin (Hirata, Y., et al., Hypertension 25:790–795 (1995); and Ebara, T., et al., Eur. J. Pharmacol. 263:69–73)). Adrenomedullin is a bronchodilator, and it modulates release of pituitary and vasoactive hormones (Tian, Q., et al., Can. J. Physiol. Pharmacol. 73:1065–1069 (1995); Kohno, M., et al., Hypertension 25:1185–1190 (1995); and Yamaguchi, T., et al., Life Sci. 56:379–387 (1994)).

SUMMARY OF THE INVENTION

The present invention relates to a method for promoting bone growth in a patient (e.g., a mammal such as a human). The method includes the step of administering a therapeutically effective amount of adrenomedullin or an adrenomedullin agonist to said patient. The adrenomedullin or adrenomedullin agonist may be administered parenterally, e.g., administered intravenously, subcutaneously, or by implantation of a sustained release formulation. The patient may be suffering from a disease associated with excessive resorption or breakdown of bone tissue such as osteoporosis or Paget's disease. The patient may also be suffering from bone losses as a result of immobility, bone fractures, malignancy, endocrine disorders, autoimmune arthritis, or drug use. The patient may also be undergoing a treatment (e.g., corticosteroid treatment, bone marrow transplantation, or oopherectomy) known to result in bone loss.

Definition of "adrenomedullin agonist" will be defined below. A therapeutically effective amount depends upon the condition being treated, the route of administration chosen, and the specific activity of the compound used and ultimately will be decided by the attending physician or veterinarian. In one embodiment, the adrenomedullin agonist is administered to the patient until the patient's bone mass has been restored to normal levels. Thus, the duration of the administration may be dependent upon the severity of the patient's bone loss.

The adrenomedullin or adrenomedullin agonist may be injected parenterally, e.g., intravenously, into the bloodstream of the subject being treated. However, it will be readily appreciated by those skilled in the art that the route, such as intravenous, subcutaneous, intramuscular, intraperitoneal, enterally, transdermally, transmucously, sustained released polymer compositions (e.g., a lactide polymer or copolymer microparticle or implant), profusion, pulmonary (e.g., inhalation), nasal, oral, etc., will vary with the condition being treated and the activity and bioavailability of the adrenomedullin or adrenomedullin agonist being used.

While it is possible for the adrenomedullin or adrenomedullin agonist to be administered as the pure or substantially pure compound, it may also be presented as a pharmaceutical formulation or preparation. The formulations to be used in the present invention, for both humans and animals, comprise any of the adrenomedullin or adrenomedullin agonists to be described below, together with one or more pharmaceutically acceptable carriers thereof, and optionally other therapeutic ingredients.

The carrier must be "acceptable" in the sense of being compatible with the active ingredient(s) of the formulation (e.g., capable of stabilizing peptides) and not deleterious to the subject to be treated. Desirably, the formulation should not include oxidizing agents or other substances with which peptides are known to be incompatible. For example, adrenomedullin or adrenomedullin agonists in the cyclized form (e.g., internal cysteine disulfide bond) are oxidized; thus, the presence of reducing agents as excipients could lead to an opening of the cysteine disulfide bridge. On the other hand, highly oxidative conditions can lead to the formation of cysteine sulfoxide and to the oxidation of tryptophane. Consequently, it is important to carefully select the excipient. pH is another key factor, and it may be necessary to buffer the product under slightly acidic conditions (pH 5 to 6).

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628 and PCT Publication No. WO 94/15587.

The adrenomedullin or adrenomedullin agonist may also be administered with an bone anti-resorptive agent or another bone anabolic agent. Examples of bone resorptive agents include calcitonin, bisphosphonates (e.g., etidronate, alendronate, or pamidronate), estrogen, and analogs thereof. Examples of bone anabolic agents include parathyroid hormone, parathyroid hormone related protein, cytokines (e.g., TGF-β, IGF-1), growth hormone, ipriflavone, and analogs thereof.

In another aspect, the invention features a peptide consisting of between 30 and 26 amino acids and comprising the sequence adrenomedullin(27–52)(SEQ ID NO:1) wherein the carboxy terminal is a free acid or amidated. Examples of such peptides include adrenomedullin(27–52)(SEQ ID NO:1); adrenomedullin(26–52) (SEQ ID NO:2); adrenomedullin(25–52)(SEQ ID NO:3); adrenomedullin (24–52)(SEQ ID NO:4); or adrenomedullin(23–52)(SEQ ID NO:5) wherein the carboxy terminal is amidated. Peptides of this invention are described herein, for example, by the following format: adrenomedullin(13–52) (SEQ ID NO:11). The numbers between the parentheses refer to the number of amino acids present in the peptide, e.g., the forty amino acid fragment between the serine residue at position 13 and the amidated tyrosine residue at position 52 of adrenomedullin. The sequence of adrenomedullin is listed in FIG. 1 of European Patent Application No. 622,458 A2.

Other features and advantages of the invention will be apparent from the following description of the preferred embodiments and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

ADRENOMEDULLIN AND ADRENOMEDULLIN AGONISTS

Adrenomedullin is a 52-amino acid having an amidated C-terminus. Many analogs, e.g., carboxy terminal fragments, have been prepared, such as adrenomedullin (15–52)(SEQ ID NO:6), adrenomedullin(1–50)(SEQ ID NO:7), adrenomedullin(11–50)(SEQ ID NO:8), adrenomedullin(22–52)(SEQ ID NO:9), adrenomedullin (40–52)(SEQ ID NO:10), adrenomedullin(13–52)(SEQ ID NO:11), adrenomedullin(47–52)(SEQ ID NO:12), and adrenomedullin(45–52)(SEQ ID NO:13). See European Patent No. 622,458 A2; Lin, et al., Eur. J. Pharmacol. 260:1–4 (1990); and Santiago, J. A., et al., Eur. J. of Pharmacology 272:115–118 (1995). What is meant by an adrenomedullin agonist is a compound which (1) has a high affinity (e.g., a Ki of less than 1 $\mu$M) for the adrenomedullin receptor (as defined by the receptor binding assay described in Owji, et al., Endocrinology 136(5):2128 (1995)) and (2) promotes the proliferation of osteoblast cells (as defined below in the osteoblast proliferation assays).

SYNTHESIS

The synthesis of short amino acid sequences is well established in the peptide art. See, e.g., Stewart, et al., Solid Phase Peptide Synthesis (2d ed., 1984). The following is the synthesis of adrenomedullin (27–52)(SEQ ID NO:1). Other such adrenomedullin agonists can be prepared by making appropriate modifications, within the ability of someone of ordinary skill in the filed of the synthetic method described herein.

Benzhydrylamine-polystyrene resin (Advanced ChemTech, Inc., Louisville, Ky.) (0.6 g, 0.25 mmole) in the chloride ion form was placed in the reaction vessel of an Advanced ChemTech peptide synthesizer programmed to perform the following reaction cycle: (a) methylene chloride; (b) 33% trifluoroacetic acid in methylene chloride (2 times for 1 and 15 min each); (c) methylene chloride; (d) ethanol; (e) methylene chloride; and (f) 10% diisopropylethylamine in methylene chloride.

The neutralized resin was stirred with Boc-Tyr(2,6-dichlorobenzyl) and diisopropylcarbodiimide (0.75 mmole each) in methylene chloride for 1 h and the resulting amino acid resin was then cycled through steps (a) to (f) in the above wash program. The following amino acids (0.75 mmole) were then coupled successively by the same procedure: Boc-Gly, Boc-Gln, Boc-Pro, Boc-Ser(benzyl), Boc-Ile, Boc-Lys(2-chloro-CBZ), Boc-Ser(benzyl), Boc-Arg(p-Tosyl), Boc-Pro, Boc-Ala, Boc-Ala, Boc-Val, Boc-Asn, Boc-Asp(cyclohexyl), Boc-Lys(2-chloro-CBZ), Boc-Asp (cyclohexyl), Boc-Lys(2-chloro-CBZ), Boc-Asp (cyclohexyl), Boc-Thr(benzyl), Boc-Phe, Boc-Gln, Boc-Tyr (2,6-dichlorobenzyl), Boc-Ile, Boc-Gln, Boc-His (benzyloxymethyl), and Boc-Ala. After removal of the last Boc group and washing and drying, the completed resin weighed 1.11 g. All amino acids were purchased from Bachem California, (Torrence, Calif.).

The resin described above (1.11 g, 0.25 mmole) was mixed with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen, and free peptide precipitated and was washed with ether. The crude peptide was then dissolved in a minimum volume of 2M acetic acid and eluted on a column (2.5×100 cm) of Sephadex G-50 (Pharmacia, Picataway, N.J.) using the same solvent. Fractions containing a major component, detected by ultraviolet absorption and thin layer chromatography, were then pooled, evaporated to a small volume, and applied to a column (2.5×50 cm) of Vydac octadecylsilane silica (10–15 $\mu$; Rainin, Emeryville, Calif.). This column was eluted with a linear gradient of 10–45% acetonitrile in 0.1% trifluoroacetic acid in water. Fractions were examined by thin layer chromatography (tlc) and analytical high performance liquid chromatography (hplc) and pooled to give maximum purity. Repeated lyophilization of the solution from water gave the product as the amide and as a white, fluffy power. The product is found to be homogeneous by hplc and tlc. Amino acid analysis of an acid hydrolysate confirmed the composition of the peptide. Laser desorption mass spectroscopy gave the expected molecular weight.

OSTEOBLAST CELL CULTURE

Osteoblasts were isolated by collagenase digestion from 20-day fetal rat calvariae. The calvariae were then treated twice with phosphate buffered saline (PBS; Gibco, Grand Island, N.Y.) containing 3 mM ethylene diamine-acetic acid (EDTA; Sigma Chemical Co., St. Louis, Mo.) for 15 minutes at 37° C. in a shaking water bath. After washing once in PBS, 3 ml of 1 mg/ml collagenase (Sigma Chemical Co.) was added to the calvariae for 10 minutes at 37° C. After discarding the supernatant, the calvariae were treated twice with 2 mg/ml collagenase (30 mins, 37° C.). The supernatants were then centrifuged and the cells washed in Dulbecco's Modified Eagle's Medium (DMEM; Gibco Labs, Grand Island, N.Y.) with 10% fetal calf serum (FCS), suspended in further DMEM/10% FCS, and placed in 75 cm$^3$ flasks. The cells were incubated under 5% $CO_2$ and 95% air at 37° C.

The osteoblast-like character of these cells has been established by demonstration of high levels of alkaline phosphatase and osteocalcin, and a sensitive adenylate cyclase response to parathyroid hormone and prostaglandins. Confluence was reached by 5–6 days, at which time the cells were subcultured. After trypsinization using trypsin-EDTA (0.05%/0.53 nM; Gibco Labs, Grand Island, N.Y.), the cells were rinsed in Minimal Essential Medium (MEM; Gibco Labs) with 10% FCS and resuspended in MEM with 5% FCS, then seeded ($10^5$ cells/ml) in 24-well plates (0.5 ml cell suspension per well, i.e., $5\times10^4$ cells/well).

PROLIFERATION ASSAYS

Cell proliferation studies (i.e., cell counts and thymidine incorporation) were performed both in actively-growing and growth-arrested cell populations. To produce actively-growing cells, subconfluent populations (24 hrs after subculturing) were changed to fresh MEM which contained 1% FCS and the test compounds. To produce growth-arrested cells, subconfluent populations were changed to serum-free medium with 0.1% bovine serum albumin plus the test compounds.

A. Cell Counts:

The effect of adrenomedullin on proliferation of fetal rat osteoblast-like cells was first assessed by the measurement of cell numbers. Cell counts were analyzed at 6, 24, and 48 hours after addition of the test compound or vehicle. The cell numbers were determined after removing cells from the wells by exposure to trypsin/EDTA (0.05%/0.53 mM) for 5 minutes at 37° C. Counting was performed in a hemocytometer chamber. Results were expressed per well.

Treatment with adrenomedullin for 24 hours, in cultures grown in medium containing 1% FCS, produced a dose-dependent increase in actively-growing osteoblasts. A significant increase was observed at adrenomedullin concentrations of $10^{-12}$M and greater. This stimulation was maintained for at least 48 hours.

To determine whether proliferation in response to adrenomedullin was dependent on the basal growth rate of the cells, these experiments were repeated in growth-arrested osteoblast preparations. The time-course of the increase in cell number in response to adrenomedullin ($1^{-10}$M) in these cells was similar to that seen in actively-growing cells.

Treatment for 24 hrs with the test compounds adrenomedullin(15–52)(SEQ ID NO:6), adrenomedullin (22–52)(SEQ ID NO:9), and adrenomedullin(27–52)(SEQ ID NO:1) produced similar degrees of proliferation to that of the full length adrenomedullin.

B. DNA Synthesis:

The effect of adrenomedullin on DNA synthesis in osteoblasts was then assessed by the measurement of [$^3$H]-thymidine incorporation into isolated fetal rat osteoblast-like cells. [$^3$H]-thymidine incorporation into actively-growing and growth-arrested cells was assessed by pulsing the cells with [$^3$H]-thymidine (1 $\mu$Ci/ml) (Amersham, Arlington Heights, Ill.) two hours before the end of the experimental incubation. The experiment was terminated at 6, 24, or 48 hours by washing the cells in MEM with cold thymidine followed by 10% trichloroacetic acid. The precipitate was washed twice with ethanol:ether (3:1), and the wells were desiccated at room temperature. The residue was redissolved in 0.5M KOH at 85° C. for 30 mins, neutralized with 1M HCl, and an aliquot counted for radioactivity. Results were expressed as cpm per well.

Treatment with adrenomedullin ($10^{-10}$M) for 24 hours significantly stimulated [$^3$H]-thymidine incorporation into both actively-growing and growth-arrested cells.

BONE ORGAN CULTURE

Bone resorption studies were carried out in neonatal mouse calvariae as previously described (Reid, et al., Endocrinology 126:1416–1420 (1990)). Mice were injected subcutaneously with 5 $\mu$Ci $^{45}$Ca (Amersham) at 2 days of age, and hemi-calvariae were dissected out 4 days later. Hemi-calvariae were pre-incubated for 24 hours in medium 199 (Gibco BRL, Grand Island, N.Y.) with 0.1% bovine serum albumin, then changed to fresh medium containing adrenomedullin or control vehicle. Incubation was continued for a further 48 hours. In the last 4 hours of incubation [$^3$H]-thymidine was incorporated into the organ cultures as described previously (Lowe, et al., Calif. Tissue Int. 49-394–397 (1991)). There were 5–7 calvariae in each group.

There was no significant change in $^{45}$Ca release from prelabeled calvariae treated for 48 hours with adrenomedullin at concentrations of $10^{-7}$M to $10^{-10}$M indicating that adrenomedullin did not stimulate bone resorption. In contrast, [$^3$H]-thymidine incorporation was significantly increased in the same experiments indicating that adrenomedullin stimulated bone growth.

DESCRIPTION OF THE PREFERRED EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of promoting bone growth, said method comprising administering to a patient an effective amount of adrenomedullin or an adrenomedullin agonist, wherein said adrenomedullin agonist is a peptide consisting of between 30 and 26 amino acids and comprising the sequence adrenomedullin(27–52) (SEQ ID NO:1), wherein the carboxy terminus of said adrenomedullin or adrenomedullin agonist is a free acid or amidated and said patient suffers from osteoporosis, or a condition characterized by loss of bone, breakdown of bone tissue, or excessive resorption of bone tissue.

2. A method of claim 1, wherein said method comprises administering an adrenomedullin agonist.

3. A method of claim 1, wherein said patient suffers from osteoporosis.

4. A method of claim 2, wherein said patient suffers from osteoporosis.

5. A method of claim 1, wherein said adrenomedullin or adrenomedullin agonist is administered nasally or pulmonarily.

6. A method of claim 1, wherein said adrenomedullin or adrenomedullin agonist is administered parenterally.

7. A method of claim 5, wherein said adrenomedullin is in a sustained release formulation.

8. A method of claim 2, wherein said adrenomedullin agonist is administered nasally or pulmonarily.

9. A method of claim 2, wherein said adrenomedullin agonist is administered parenterally.

10. A method of claim 9, wherein said adrenomedullin is in a sustained release formulation.

11. A method of claim 2, wherein said adrenomedullin agonist is in a sustained release formulation.

12. A method of claim 3, wherein said adrenomedullin or adrenomedullin agonist is administered nasally or pulmonarily.

13. A method of claim 3, wherein said adrenomedullin or adrenomedullin agonist is administered parenterally.

14. A method of claim 13, wherein said adrenomedullin or adrenomedullin agonist is in a sustained release formulation.

15. A method of claim 4, wherein said adrenomedullin or adrenomedullin agonist is administered nasally or pulmonarily.

16. A method of claim 4, wherein said adrenomedullin or adrenomedullin agonist is administered parenterally.

17. A method of claim 16, wherein said adrenomedullin is in a sustained release formulation.

18. A peptide consisting of between 30 and 26 amino acids and comprising the sequence adrenomedullin(27–52) (SEQ ID NO:1) wherein the carboxy terminus of said peptide is a free acid or amidated.

19. A peptide of claim 18, wherein said peptide is adrenomedullin(27–52)(SEQ ID NO:1); adrenomedullin (26–52)(SEQ ID NO:2); adrenomedullin(25–52)(SEQ ID NO:3); adrenomedullin(24–52)(SEQ ID NO:4); or adrenomedullin(23–52)(SEQ ID NO:5) wherein the carboxy terminal thereof is amidated.

20. A method of claim 2, wherein said agonist is adrenomedullin(27–52) (SEQ ID NO:1), adrenomedullin (26–52) (SEQ ID NO:2), adrenomedullin(25–52) (SEQ ID NO:3), adrenomedullin(24–52) (SEQ ID NO:4), or adrenomedullin(23–52) (SEQ ID NO:5), wherein the carboxy terminal thereof is amidated.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ala His Gln Ile Tyr Gln Phe Thr Asp Lys Asp Lys Asp Asn Val Ala
 1               5                  10                  15
Pro Arg Ser Lys Ile Ser Pro Gln Gly Tyr
            20                  25
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Leu Ala His Gln Ile Tyr Gln Phe Thr Asp Lys Asp Lys Asp Asn Val
 1               5                  10                  15
Ala Pro Arg Ser Lys Ile Ser Pro Gln Gly Tyr
                20                  25
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Lys Leu Ala His Gln Ile Tyr Gln Phe Thr Asp Lys Asp Lys Asp Asn
 1               5                  10                  15
Val Ala Pro Arg Ser Lys Ile Ser Pro Gln Gly Tyr
                20                  25
```

( 2 ) INFORMATION FOR SEQ ID NO:4:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Gln Lys Leu Ala His Gln Ile Tyr Gln Phe Thr Asp Lys Asp Lys Asp
 1               5                  10                  15
Asn Val Ala Pro Arg Ser Lys Ile Ser Pro Gln Gly Tyr
                20                  25
```

( 2 ) INFORMATION FOR SEQ ID NO:5:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Val Gln Lys Leu Ala His Gln Ile Tyr Gln Phe Thr Asp Lys Asp Lys
 1               5                  10                  15
Asp Asn Val Ala Pro Arg Ser Lys Ile Ser Pro Gln Gly Tyr
            20                  25                  30
```

( 2 ) INFORMATION FOR SEQ ID NO:6:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Gly Cys Arg Phe Gly Thr Cys Thr Val Gln Lys Leu Ala His Gln Ile
 1               5                  10                  15
Tyr Gln Phe Thr Asp Lys Asp Lys Asp Asn Val Ala Pro Arg Ser Lys
                20                  25                  30
Ile Ser Pro Gln Gly Tyr
            35
```

( 2 ) INFORMATION FOR SEQ ID NO:7:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Tyr Arg Gln Ser Met Asn Asn Phe Gln Gly Leu Arg Ser Phe Gly Cys
 1               5                  10                  15
Arg Phe Gly Thr Cys Thr Val Gln Lys Leu Ala His Gln Ile Tyr Gln
                20                  25                  30
Phe Thr Asp Lys Asp Lys Asp Asn Val Ala Pro Arg Ser Lys Ile Ser
                35                  40                  45
Pro Gln
    50
```

( 2 ) INFORMATION FOR SEQ ID NO:8:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Leu Arg Ser Phe Gly Cys Arg Phe Gly Thr Cys Thr Val Gln Lys Leu
 1               5                  10                  15
Ala His Gln Ile Tyr Gln Phe Thr Asp Lys Asp Lys Asp Asn Val Ala
                20                  25                  30
```

Pro Arg Ser Lys Ile Ser Pro Gln
35                    40

(2) INFORMATION FOR SEQ ID NO:9:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:9:

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

(2) INFORMATION FOR SEQ ID NO:10:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:10:

Asn Val Ala Pro Arg Ser Lys Ile Ser Pro Gln Gly Tyr
1               5                   10

(2) INFORMATION FOR SEQ ID NO:11:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:11:

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Arg
            20                  25                  30

Ser Lys Ile Ser Pro Gln Gly Tyr
35                    40

(2) INFORMATION FOR SEQ ID NO:12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:12:

Ile Ser Pro Gln Gly Tyr
1               5

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: linear -continued (ii) MOLECULE TYPE: peptide (xi) SEQUENCE DESCRIPTION: SEQ ID NO:13:

```
Ser  Lys  Ile  Ser  Pro  Gln  Gly  Tyr
 1              5
```